(12) United States Patent
Piao et al.

(10) Patent No.: US 8,819,175 B2
(45) Date of Patent: Aug. 26, 2014

(54) MEDICAL-INFORMATION MANAGEMENT SYSTEM AND MEDICAL-INFORMATION MANAGEMENT METHOD

(75) Inventors: Longxun Piao, Nasushiobara (JP); Masaaki Nagashima, Nasushiobara (JP); Kousuke Sakaue, Nasushiobara (JP); Minoru Yagi, Otawara (JP); Satoshi Ikeda, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 156 days.

(21) Appl. No.: 13/398,134

(22) Filed: Feb. 16, 2012

(65) Prior Publication Data
US 2012/0215884 A1    Aug. 23, 2012

(30) Foreign Application Priority Data
Feb. 23, 2011    (JP) .................................. 2011-037262

(51) Int. Cl.
*G06F 15/16*    (2006.01)
(52) U.S. Cl.
USPC .................................. 709/217; 705/3; 713/1
(58) Field of Classification Search
CPC .................................................. G06F 19/327
USPC ............................................................ 709/217
See application file for complete search history.

(56) References Cited

FOREIGN PATENT DOCUMENTS

| JP | 2003-6341 | 1/2003 |
|---|---|---|
| JP | 2008-284294 | 11/2008 |

*Primary Examiner* — Hamza Algibhah
(74) *Attorney, Agent, or Firm* — Oblon, Spivak, McClelland, Maier & Neustadt, L.L.P.

(57) ABSTRACT

A medical-information management system, connected via a network to multiple servers including medical-information memories storing medical information, which manages the medical information by distributing the medical information of multiple medical facilities to the multiple servers, comprises operating-time-information memory, operational-status analysis part, and medical-information transmission part. The operating-time-information memory stores respective operating times of each of multiple servers. The management-information memory stores management information indicating servers in which the medical information is stored. The operational-status analysis part provides notification of other servers other than a first server based on information indicating operating times. The medical-information transmission part determines a second server for temporarily saving the medical information from among the notified other servers, and transmits the medical information to the second server.

15 Claims, 13 Drawing Sheets

| FACILITY ID (c10) | OPERATION START TIME (c11) | OPERATION END TIME (c12) | START DATE (c13) | END DATE (c14) |
|---|---|---|---|---|
| 1A | 9:00 | 18:00 | 2000/01/01 | 2015/12/31 |
| 1B | 12:00 | 24:00 | 2006/01/01 | 2020/12/31 |
| 1C | 8:00 | 17:00 | 2005/01/01 | 2020/12/31 |
| 1D | 0:00 | 22:00 | 2000/01/01 | 2015/12/31 |
| 1E | 12:00 | 24:00 | 2009/01/01 | 2025/12/31 |
| 1F | 0:00 | 18:00 | 2009/01/01 | 2025/12/31 |

FIG. 5

| PATIENT ID | TREATMENT INFORMATION ID | REGISTRATION DATE | FACILITY ID |
|---|---|---|---|
| P1000 | S001 | 2009/10/23 | 1A |
| P1000 | S002 | 2010/03/15 | 1B |
| P1000 | S003 | 2010/05/21 | 1A |
| P2000 | S001 | 2008/11/25 | 1D |
| P2000 | S002 | 2009/02/28 | 1B |
| P3000 | S001 | 2009/12/11 | 1C |
| P4000 | S001 | 2008/01/05 | 1A |

FIG. 6

| PATIENT ID (c20) | FACILITY ID (c10) | INTRA-FACILITY ID (c30) |
|---|---|---|
| P1000 | 1A | 10 |
| P1000 | 1B | 123 |
| P1000 | 1C | 700234 |
| P1000 | 1D | a12 |
| P2000 | 1A | 15 |
| P2000 | 1B | 176 |
| P2000 | 1C | 700432 |
| P2000 | 1D | a23 |

| PATIENT ID (INTRA-FACILITY ID) c30 | TREATMENT INFORMATION ID c21 | PATIENT NAME c31 | AGE c32 | ... | CACHE FLAG c40 |
|---|---|---|---|---|---|
| 10 | S001 | AAA BBB | 29 | ... | 0 |
| 12 | S008 | CCC DDD | 35 | ... | 0 |
| 15 | S010 | EEE FFF | 42 | ... | 1 |
| 17 | S018 | GGG HHH | 20 | ... | 1 |

D40

MEDICAL-INFORMATION MANAGEMENT SYSTEM AND MEDICAL-INFORMATION MANAGEMENT METHOD

CROSS-REFERENCE TO RELATED APPLICATION

This application is based upon and claims the benefit of priority from Japanese Patent Application No. 2011-037262, filed Feb. 23, 2011; the entire contents of which are incorporated herein by reference.

FIELD

The embodiment of the present invention is related to a technology for a medical-information management system that performs transmission and reception of medical information between multiple servers.

BACKGROUND

There exist regional collaboration systems that enable multiple medical institutions within a prescribed region to share medical information (e.g., medical records and radiograph interpretation reports of patients, etc.) managed and stored by each medical institution. The regional collaboration system provides a datacenter to which multiple medical institutions in a region can refer, and this datacenter stores the location (i.e., the medical institution) of each item of medical information as management information. Based on this management information, medical institutions in the region acquire medical information created by other medical institutions from those medical institutions via a network. In this way, in a regional collaboration system, when multiple items of medical information are distributed and managed across each medical institution, it is possible for multiple medical institutions in the region to collaborate by sharing medical information via a network.

On the other hand, the multiple medical institutions in the region may not necessarily have the same business hours. Therefore, the operating times of the servers managing the medical information may differ for each medical institution. As a result, during the non-operating time of a server, it is difficult for another medical institution to use the medical information stored in that server. Anticipating these non-operating times, there are methods of preliminarily storing copies of the medical information stored in each server in each medical institution, allowing the copies of the medical information to be referred to in the operating hours. However, enormous storage areas would be required for each medical institution in the region to store all of the copies of the medical information stored in all of the medical institutions. In particular, because the number of items of medical information stored in the medical institutions in a region increases exponentially as the number of medical institutions increases, it is extremely difficult to store copies of all medical information in each medical institution.

BRIEF DESCRIPTION OF THE DRAWINGS

FIG. 4 is an example of the data structure of operation information.

FIG. 5 is an example of the data structure of management information.

FIG. 6 is an example of the data structure of management information.

FIG. 7 is an example of the data structure of medical information.

DETAILED DESCRIPTION

Figure 1:
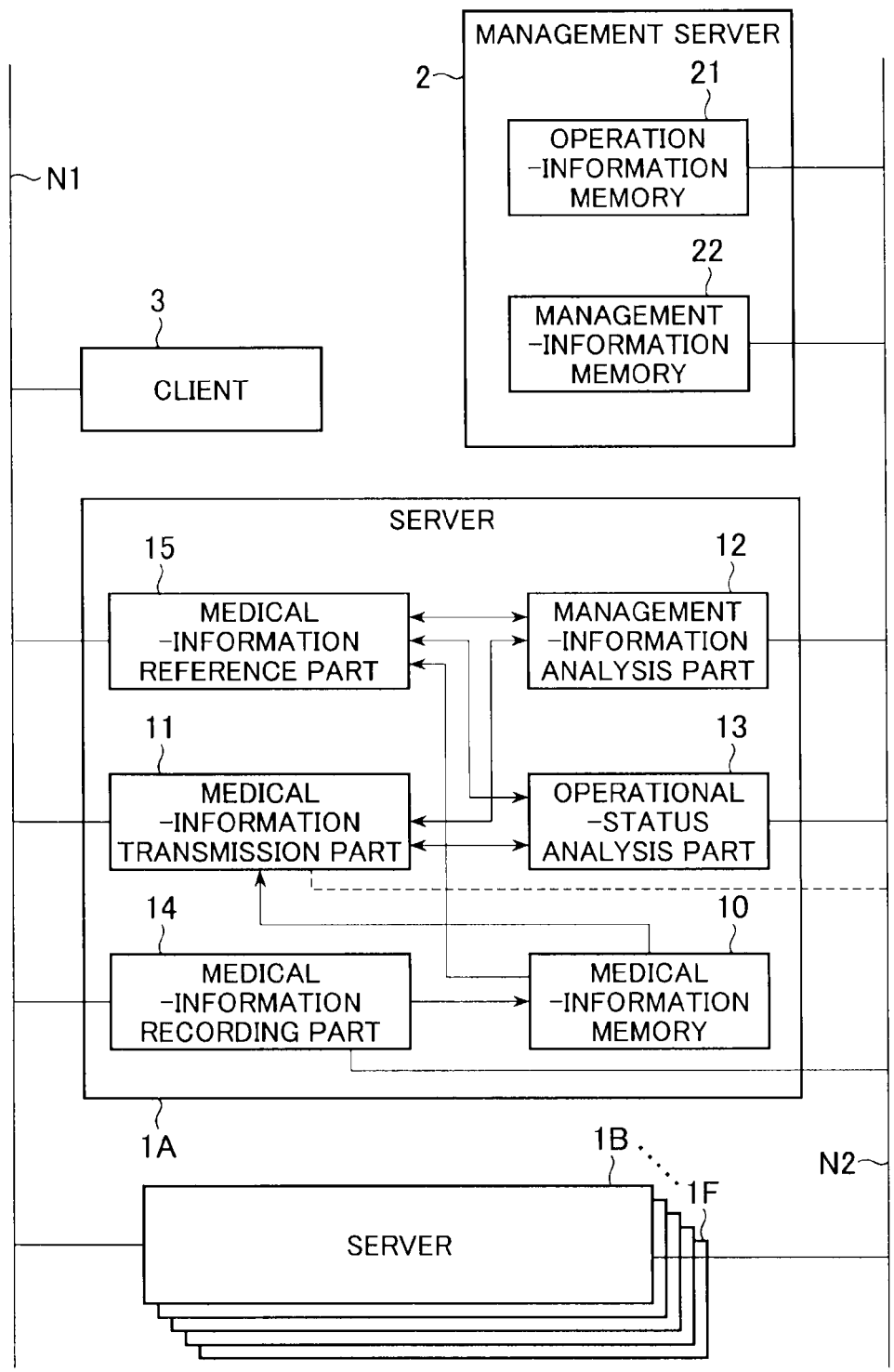
FIG. 1 is a block diagram of a medical-information management system according to a first embodiment.

To achieve the above objective, a first mode of the present embodiment is a medical-information management system that is connected via a network to multiple servers including medical-information memories storing medical information, and that distributes the medical information of multiple medical facilities to the multiple servers and manages the medical information. The medical-information management system includes an operating-time-information memory, an operational-status analysis part, and a medical-information transmission part. The operating-time-information memory stores the respective operating times of each of the multiple servers. The management-information memory stores management information indicating the servers in which the medical information is stored. The operational-status analysis part provides notification of other servers different from a first server based on information related to operating times. The medical-information transmission part determines a second server for temporarily saving the medical information stored in the first server from among the notified other servers, and transmits the medical information stored in the medical-information memory of the first server to the second server.

Moreover, a second mode of the present invention is a medical-information management system that is connected via a network to multiple servers including medical-information memories storing medical information, and that distributes the medical information of multiple medical facilities to the multiple servers and manages the medical information. The medical-information management system includes a performance-information calculation part and a medical-information transmission part. The performance-information calculation part obtains the processing-load information of the multiple servers. The management-information memory stores management information indicating the servers in which the medical information is stored. Based on the processing-load information, the medical-information transmission part determines a second server for temporarily saving the medical information stored in a first server, and transmits the medical information stored in the medical-information memory of the first server to the second server.

Moreover, a third mode of the present invention is a medical-information management system including: multiple medical-information servers including medical-information memories storing medical information; and a management information server. The management information server manages the information of multiple medical facilities, and stores management information indicating the medical-information servers in which the medical information is stored. At least one of either the medical-information servers or the management information server includes an operating-time-information memory, an operational-status analysis part, and a medical-information transmission part. The operating-time-information memory stores information regarding the operating times of the multiple medical-information servers. Based on the information regarding operating times, the operational-status analysis part provides notifications of other servers different from a first medical-information server. From among the notified other servers, the medical-information transmission part determines a second medical-information server for temporarily saving the medical information stored in the first medical-information server, and transmits the medical information stored in the medical-information server of the first medical-information server to the second medical-information server.

Moreover, a fourth mode of the present embodiment is a medical-information management system including: multiple medical-information servers including medical-information memories storing medical information; and a management information server. The management information server manages the information of multiple medical facilities, and stores management information indicating the medical-information servers in which the medical information is stored. At least one of either the medical-information servers or the management information server includes a performance-information calculation part and a medical-information transmission part. The performance-information calculation part obtains the processing-load information of the multiple medical-information servers. The medical-information transmission part determines a second medical-information server for temporarily saving the medical information stored in a first medical-information server based on the processing-load information, and transmits the medical information stored in the medical-information memory of the first medical-information server to the second medical-information server.

Moreover, a fifth mode of the present embodiment is a medical-information management method based on a medical-information management system that is connected via a network to multiple servers including medical-information memories storing medical information and that distributes multiple items of medical information to the multiple servers and manages the medical information. The medical-information management method includes a first-group identification step, a second-group identification step, a transmission step, a third-group identification step, a fourth-group identification step, and a reference step. In the first-group identification step, based on the pre-stored operating times of multiple servers, the operating time of a first server included in the multiple servers is compared with the operating times of other servers other than the first server, and a first group including servers operating when the first server is not operating is identified from among the other servers. In the second-group identification step, based on pre-stored management information indicating the servers storing the medical information, a second group including servers in which a first item of medical information is not stored is identified from among the multiple servers. In the transmission step, a server included in both the first group and the second group is identified as the second server, and the first item of medical information is transmitted to the second server. In the third-group identification step, upon receiving a retrieval request for the first item of medical information, a third group including servers operating at the time at which the request was received is identified based on the operating times of the multiple servers. In the fourth-group identification step, based on the management information, a fourth group including servers in which the first item of medical information is stored is identified. In the reference step, one server included in both the third group and the fourth group is identified as the third server, and the first item of medical information is transmitted to the third server.

Moreover, a sixth mode of the present embodiment is a medical-information management system that is connected via a network to multiple servers including medical-information memories storing medical information, and that distributes the multiple items of medical information to the multiple servers and manages the medical information. The medical-information management system includes an operating-time-information memory and an operational-status analysis part. The operating-time-information memory stores the respective operating times of each of the multiple servers. The management-information memory stores management information indicating the servers in which the medical information is stored. The operational-status analysis part compares the operating time of a first server included in the multiple servers with the operating times of other servers other than the first server, and provides notification of a second server operating when the first server is not operating from among the other servers. The first server includes a medical-information transmission part. The medical-information transmission part transmits a first item of medical information stored in the medical-information memory to the second server.

First Embodiment

The configuration of the medical-information management system according to the first embodiment will be described with reference to FIG. 1. As shown in FIG. 1, the medical-information management system according to the present embodiment includes a management server 2, a client 3, and multiple servers. In the following description, the multiple servers include the servers 1A-1F. Furthermore, the servers 1A-1F represent servers that manage and store medical information provided at medical institutions such as hospitals. In the following description, one server is provided at each medical institution. Moreover, the medical-information management system according to the present embodiment has a function triggered by "the transfer of copies of medical information" and a function triggered by "the referencing of medical information". The following descriptions will be divided between these two triggers.

The management server 2 includes an operation-information memory 21 and a management-information memory 22. The term "memory" may include a storage device such as HDD and RAM. Further, the term "server" may mean a computer having CPU, RAM, HDD and a network I/F.

Figure 3:
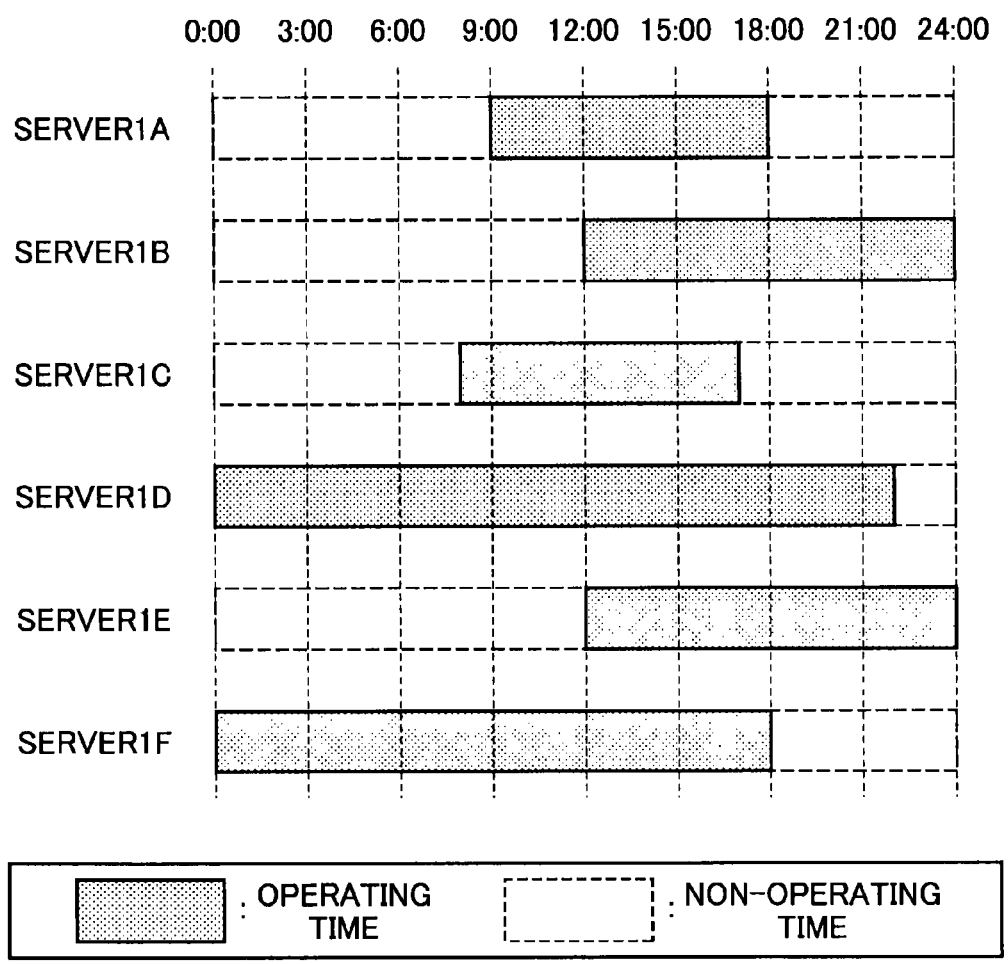
FIG. 3 is a diagram showing the operating times of various servers.

The operation-information memory 21 stores operation information D10 that has been created in advance. The operation information D10 indicates operating times during which each of the servers 1A-1F is operating. As shown in FIG. 3, the operating time of the server 1A is 9:00-18:00, and the operating time of the server 1B is 12:00-24:00. FIG. 4 is an example of the operation information D10 created based on the operating times of each server shown in FIG. 3. As shown in FIG. 4, the operation information D10 includes a facility ID (identification) c10, an operation start time c11, and an operation end time c12. The facility ID c10 indicates identification information for identifying each server. Moreover, the operation start time c11 represents the time at which each server starts operating, and the operation end time c12 indicates the time at which each server ends operation. Moreover, as shown in FIG. 4, the operation information D10 may include a start date c13 and an end date c14. The start date c13 indicates the date at which the server starts operating. Moreover, the end date c14 indicates the date at which the server ends operation. By thus providing the start date c13 and the end date c14 to the operation information D10, it becomes possible to manage the periods during which each server operates on a daily basis.

The management-information memory 22 stores data management information D20 and patient management information D30. Furthermore, the data management information D20 and the patient management information D30 may be collectively referred to as "management information".

The data management information D20 is information for identifying the servers in which each item of medical information is stored. FIG. 5 is an example of the data management information D20. The data management information D20 includes a patient ID c20, a treatment information ID c21, a registration date c22, and the facility ID c10. The patient ID c20 is identification information for uniquely identifying patients across the servers 1A-1F. Moreover, the treatment information ID c21 is information for identifying the type of treatment. In the example of FIG. 5, the patient ID c20 is combined with the treatment information ID c21 so that medical information of the patient is uniquely identified. Moreover, the registration date c22 indicates the date on which the data management information D20 was registered. Moreover, the facility ID c10 indicates the identification information of the servers that manage and store the medical information indicated by the patient ID c20 and the treatment information ID c21. For example, it is indicated that the medical information identified by the patient ID "P1000" and the treatment ID "S001" is managed and stored in the server corresponding to the facility ID "1A". Furthermore, FIG. 5 is one example. As long as the data management information D20 uniquely defines the medical information of a specific patient and identifies the server managing and storing that medical information, there are no limits to the numbers and types of items of information contained.

The patient management information D30 is information for associating and managing the patient ID c20 created in advance with an intra-facility ID c30 that is local identification information for managing patients within a server. FIG. 6 is an example of the patient management information D30. As shown in FIG. 6, the patient management information D30 includes the patient ID c20, the facility ID c10, and the intra-facility ID c30. The intra-facility ID c30 is local identification information for managing patients within the server indicated by the facility ID c10. For example, in the server corresponding to the facility ID "1A", the patient corresponding to the patient ID "P1000" is managed under the intra-facility ID (i.e., the identification information within that server) "10". In this way, the patient management information D30 allows patients to be uniquely identified across the servers 1A-1F and allows the information of that patient in each server to be identified.

The servers 1A-1F respectively include a medical-information memory 10, a medical-information transmission part 11, a management-information analysis part 12, an operational-status analysis part 13, a medical-information recording part 14, and a medical-information reference part 15.

The medical-information transmission part 11, medical-information reference part 15, and medical-information recording part 14 included in each of the servers 1A-1F are connected to the client 3 via a network N1, and transmit and receive medical information via the network N1. Moreover, the operation-information memory 21 included in the management server 2, the management-information memory 22, and the management-information analysis part 12, operational-status analysis part 13, and medical-information recording part 14 included in each of the servers 1A-1F are connected via a network N2, and transmit and receive operation information and management information via the network N2. Furthermore, if the relationship between each configuration and the information transmitted and received between these configurations is maintained, each configuration may be connected via a single network that is not divided between the network N1 and the network N2. Furthermore, by dividing the network N1 from the network N2, even if, for example, congestion occurs in the network N1 due to an increase in the transmission and reception of medical information, it is possible to transmit and receive operation information and management information without being affected by this congestion. Furthermore, the servers 1A-1F represent the "medical-information servers".

The medical-information memory 10 stores the medical information D40 created for each patient, such as medical records and radiograph interpretation reports, associated with the information of that patient. FIG. 7 is an example of the medical information D40. As shown in FIG. 7, the medical information D40 includes the intra-facility ID c30 for identifying patients within a server, the treatment information ID c21, information of that patient (e.g., patient name c31 and age c32), and a cache flag c40. The medical information stored in the medical-information memory 10 is uniquely identified within the server based on the intra-facility ID c30 and the treatment information ID c21.

Moreover, as will be described in detail later, the medical-information management system according to the present embodiment, causes copies of the medical information managed and stored in a specific server to be stored in other servers. As a result, if the medical information stored in one server cannot be referenced, the medical-information management system can refer to copies of that medical information that are stored in other servers. For this reason, by providing the medical information D40 with a cache flag c40, it is possible to identify whether the medical information has been created within that server or is a copy transferred from another server, based on this cache c40. For example, if the medical information has been created within that server, the cache flag c40 is set to "0", while if it is a copy transferred from another server, the cache flag c40 is set to "1". The cache flag is set by the medical-information recording part 14. The details of the medical-information recording part 14 will be described later. Furthermore, medical information created within a server may be differentiated from copies transferred from another server, not only by the cache flag c40, but by, for example, dividing the storage areas.

Furthermore, the medical-information transmission part 11, the management-information analysis part 12, the operational-status analysis part 13, the medical-information recording part 14, and the medical-information reference part 15 respectively have different configurations and the operations between cases of transferring copies of medical information and cases of referencing medical information. Thus, by separating "transferring of copies of medical information"

from "referencing of medical information", the following description focuses on the configurations that operate based on each trigger.

(Transferring of Copies of Medical Information)

Figure 2:
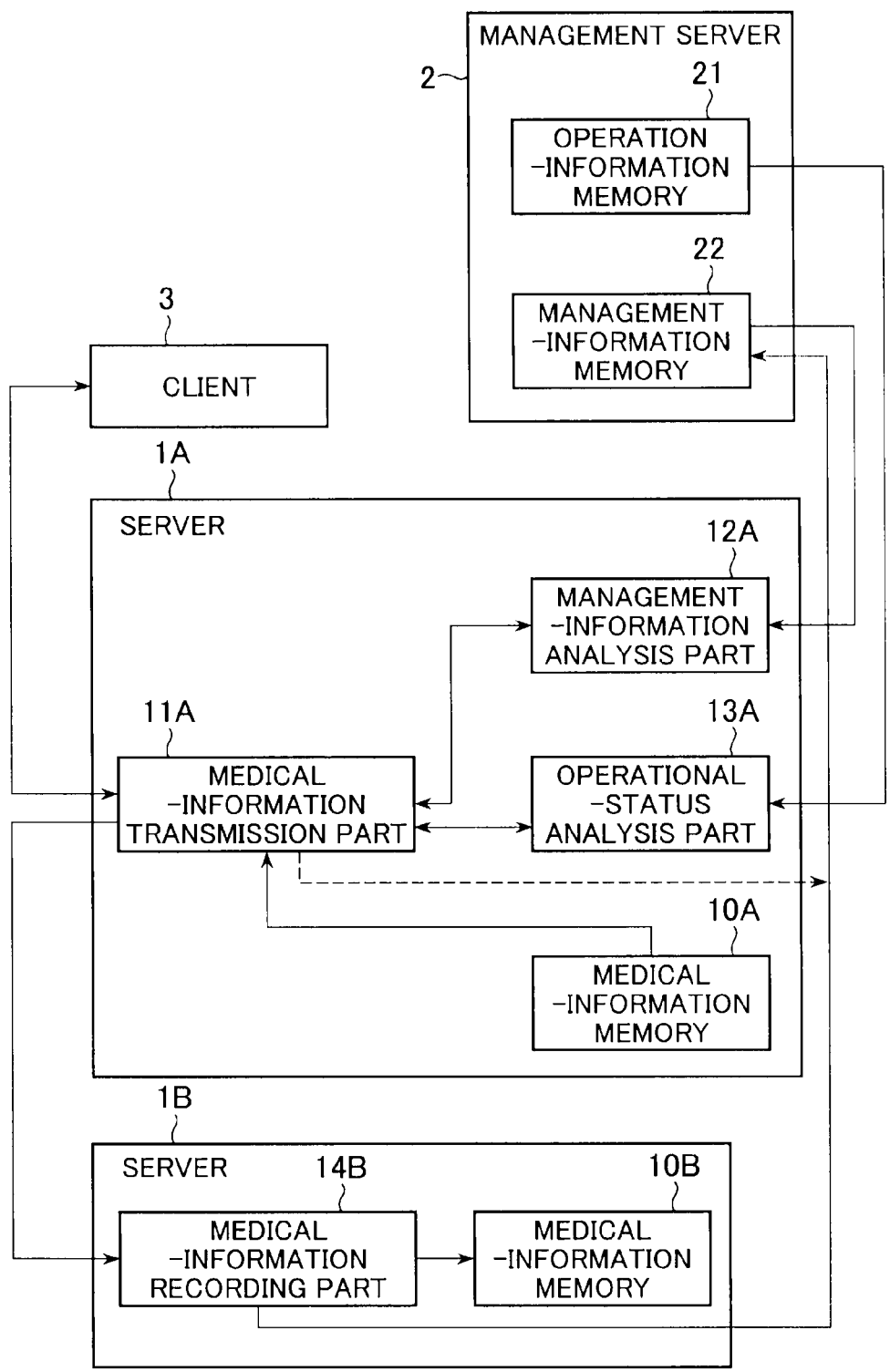
FIG. 2 is a block diagram of a medical-information management system focusing on the transfer of copies of medical information.

First, configurations for operation in cases of transferring copies of medical information will be described with reference to FIG. 2. FIG. 2 is a block diagram of a medical-information management system focusing on transfers of copies of medical information. FIG. 2 shows a case of transferring a copy of medical information from the server 1A to the server 1B. In FIG. 2, the medical-information transmission part 11A, management-information analysis part 12A, the operational-status analysis part 13A, and the medical-information memory 10A respectively represent the medical-information transmission part 11, the management-information analysis part 12, the operational-status analysis part 13, and the medical-information memory 10 included in the server 1A. Moreover, the medical-information recording part 14B and the medical-information memory 10B respectively represent the medical-information recording part 14 and the medical-information memory 10 of the server 1B. Furthermore, the medical-information transmission part 11 represents the "medical-information transmission part".

The medical-information transmission part 11A receives an instruction indicating the transfer of medical information from the operator. Upon receiving this instruction, the medical-information transmission part 11A identifies the medical information (hereinafter also referred to as the "transfer subject") to be transferred to another server from among the medical information stored in the medical-information memory 10A. An example of this identification method is described below. For example, the medical-information transmission part 11A receives an instruction regarding the medical information to be transferred to the other server from the operator. In this case, the medical-information transmission part 11A defines the medical information of the instruction as the transfer subject. In another example, the medical-information transmission part 11A receives conditions for the medical information to be transferred to the other server that have been created based on the information (e.g., patient information such as age or sex, etc.) recorded in the medical information from the operator. In this case, the medical-information transmission part 11A defines medical information matching these conditions (e.g., elderly patients, or patients receiving regular medical checkups, etc.) as the transfer subject. Moreover, the medical-information transmission part 11A may identify the transfer subject according to the severity of the symptoms of the patient. Specifically, keywords indicating disease names and symptoms that are used as medical information are weighted in advance. The medical-information transmission part 11A extracts these keywords from each item of medical information, identifies the severity of the symptoms based on the number of extracted keywords or the weightings of those keywords, and identifies, for example, the medical information of patients with the most severe symptoms as the transfer subject. Moreover, the transfer subject may be identified based on the volume of medical information or the updated volume (the volume of updated information) of medical information. Moreover, by associating the medical information with history information indicating the history of accesses to that medical information, it is also possible to identify the medical information to be the subject of a transfer based on this history information. In this case, the medical-information transmission part 11A refers to the history information associated with each item of medical information, and defines medical information with an access frequency exceeding a threshold value defined in advance by the operator as the transfer subject. In this way, the medical-information transmission part 11A identifies medical information that has a high probability of being used as the transfer subject.

Next, the medical-information transmission part 11A outputs information for identifying the transfer subject (i.e., the patient ID c20 and the treatment information ID c21) to the management-information analysis part 12A. As this response, the medical-information transmission part 11A receives a list of servers in which the transfer subject is not managed and stored from the management-information analysis part 12A. Moreover, the medical-information transmission part 11A causes the operational-status analysis part 13A to output a list of servers operating during the non-operating time of the server 1A. Furthermore, the operations of the management-information analysis part 12A and the operational-status analysis part 13A will be described later.

The medical-information transmission part 11A identifies servers included in both the list of servers in which the transfer subject is not managed and stored as well as the list of servers operating during the non-operating time of the server 1A as transfer destination servers. In other words, transfer destination servers indicate servers that are operating during the non-operating time of the server 1A and in which the transfer subject is not managed and stored. In the following description, the medical-information transmission part 11A has identified the server 1B as the transfer destination server.

The medical-information transmission part 11A creates a copy of the transfer subject, and transmits this copy to the medical-information recording part 14B of the server 1B.

The medical-information recording part 14B receives the copy of the transfer subject from the medical-information transmission part 11A. Upon setting the cache flag c40 to "1", which indicates a copy transferred from another server, the medical-information recording part 14B stores the copy in the medical-information memory 10B.

Moreover, based on the patient ID c20 and treatment information ID c21 indicating the medical information that is the transfer subject, as well as on the facility ID c10 indicating the server itself (i.e., the server 1B), the medical-information recording part 14B creates a row of data management information for the transfer subject. The medical-information recording part 14B adds the created row of data management information to the data management information D20 stored in the management-information memory 22.

Moreover, the medical-information recording part 14B refers to the patient management information D30 stored in the management-information memory 22 to confirm whether or not patient management information of the patient indicated by the patient ID c20 of the transfer subject is registered. If no patient management information has been registered, a row of patient management information is created based on the patient ID c20 of the transfer subject, the intra-facility ID c30 corresponding to the patient, and the facility ID c10 indicating the server itself (i.e., the server 1B). The medical-information recording part 14B registers the created row of patient management information in the patient management information D30 stored in the management-information memory 22.

Next, detailed operations of the management-information analysis part 12A and the operational-status analysis part 13A will be described.

The management-information analysis part 12A receives information indicating the transfer subject (i.e., the patient ID c20 and the treatment information ID c21) from the medical-information transmission part 11A. The management-information analysis part 12A refers to the data management information D20 stored in the management-information memory 22 and identifies instances of the facility ID c10 that is not associated with the information indicating the transfer subject. The management-information analysis part 12A identifies servers corresponding to the identified instances of the facility ID c10 as servers in which the transfer subject is not managed and stored. The management-information analysis part 12A creates a list of the identified servers.

Moreover, the management-information analysis part 12A refers to the patient management information D30 stored in the management-information memory 22, and identifies the intra-facility ID c30 in each server corresponding to the notified patient ID c20. The management-information analysis part 12A associates the intra-facility ID c30 in each identified server with the list of servers created based on the data management information D20. The management-information analysis part 12A outputs the list of servers, with which the intra-facility IDs c30 have been associated, to the medical-information transmission part 11A. This allows the medical-information transmission part 11A to transfer copies of the transfer subject to only the servers in which the medical information is not managed and stored. Furthermore, this list of servers represents the "second group".

The operational-status analysis part 13A receives an instruction from the medical-information transmission part 11A, and creates a list of servers operating when the server 1A is not operating (hereinafter this period is also referred to as the "non-operating time"). These operations will be described in detail using examples, with reference to FIG. 3 and FIG. 4.

First, the operational-status analysis part 13A refers to the operation information D10 stored in the operation-information memory 21. Based on the operation information D10, the operational-status analysis part 13A identifies the non-operating time of the server 1A (i.e., 18:00-9:00). Next, the operational-status analysis part 13A compares the identified non-operating time with the operating times of the other servers. Based on the results of this comparison, the operational-status analysis part 13A identifies the servers operating for the longest time within that non-operating time. In this case, as shown in FIG. 3, the servers operating for the longest time during the non-operating time of the server 1A (i.e., 18:00-9:00) are the servers 1D and 1F. The operational-status analysis part 13A selects either one or both of the servers 1D and 1F as candidates. Furthermore, if either one of the servers 1D or 1F is selected as a candidate, the number of copies to be transferred can be reduced. Thus, it is possible to ease the lack of volume in storage area caused by the storage of those copies. Moreover, by selecting both the servers 1D and 1F as candidates, the medical-information transmission part 11A transfers copies of the transfer subject to both. As a result, even if, for example, one of either the server 1D or 1F is shut down due to a malfunction, etc., it is possible to acquire the medical information from the other server. In this case, although the required storage area increases due to the increased number of copies, it is possible to keep the required storage area low compared to transferring copies to all of the servers. Moreover, the operational-status analysis part 13A may provide notification to both the servers 1D and 1F of the free space in the medical-information memory 10 and select the server with greater amount of free space as the candidate. Furthermore, the following description supposes that the server 1D is selected as the candidate.

Next, the operational-status analysis part 13A subtracts the operating time of the server 1D identified as the candidate from the non-operating time of the server 1A, so as to identify the time during which both the servers 1A and 1D are not operating as the new non-operating time. If this non-operating time is not "0", the operational-status analysis part 13A selects the servers operating for the longest time during that non-operating time as additional candidates. For example, the non-operating time during which both the server 1A and 1D are not operating is 22:00-24:00. Therefore, the operational-status analysis part 13A selects the servers 1B and 1F, as candidates. In this way, the operational-status analysis part 13A repeats the abovementioned selection of candidates either until the non-operating time during which the server 1A and all of the servers selected as candidates are not operating becomes "0" or until there are no more selectable candidates.

When the selection of candidates is complete, the operational-status analysis part 13A creates a list of servers selected as candidates, and outputs this list to the medical-information transmission part 11A. Furthermore, the operational-status analysis part 13A may create this list of servers in advance and store it in a memory. In this case, the operational-status analysis part 13A receives an instruction from the medical-information transmission part 11A, reads out the list of servers stored in the memory, and outputs the list to the medical-information transmission part 11A. Moreover, this list of servers represents the "first group".

Furthermore, by receiving an instruction from the operator, it is possible for the medical-information recording part 14B to delete the copies stored in the medical-information recording part 14B. In this case, the medical-information recording part 14B refers to the cache flag c40 included in the medical information and determines whether or not the medical information is a copy transferred from another server. If the copies are deleted, the medical-information recording part 14B deletes the data management information corresponding to the deleted copies from the data management information D20 stored in the management-information memory 22.

Moreover, the medical-information transmission part 11A that is the transfer source may operate to perform the creation and registration of the data management information of the transfer subject. In this case, the medical-information transmission part 11A creates the data management information of the transfer subject. This creation is based on the patient ID c20 and treatment information ID c21 indicating the medical information that is the transfer subject as well as on the facility ID c10 indicating the server 1B that is the transfer destination.

Moreover, the medical-information transmission part 11A may operate to transfer the transfer subject to servers in which the transfer subject is managed and stored. In this case, the medical-information recording part 14 of the server operates to overwrite medical information that is a copy transferred from the medical-information transmission part 11A and that has been stored in the medical-information memory 10 corresponding to the copy. Moreover, the medical-information recording part 14 may operate to destroy the copy without overwriting the medical information that is a transferred copy stored in the medical-information memory 10.

Figure 8:
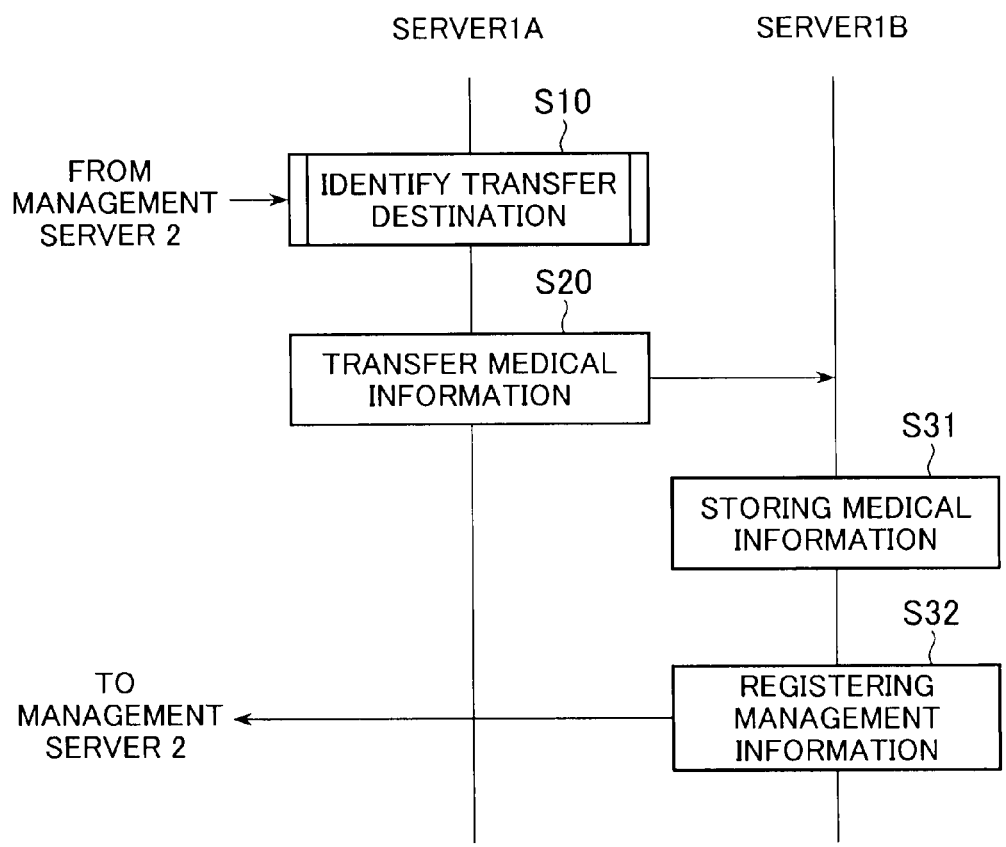
FIG. 8 is a diagram showing the flow of processes between servers involved in the transfer of medical information.
Figure 9:
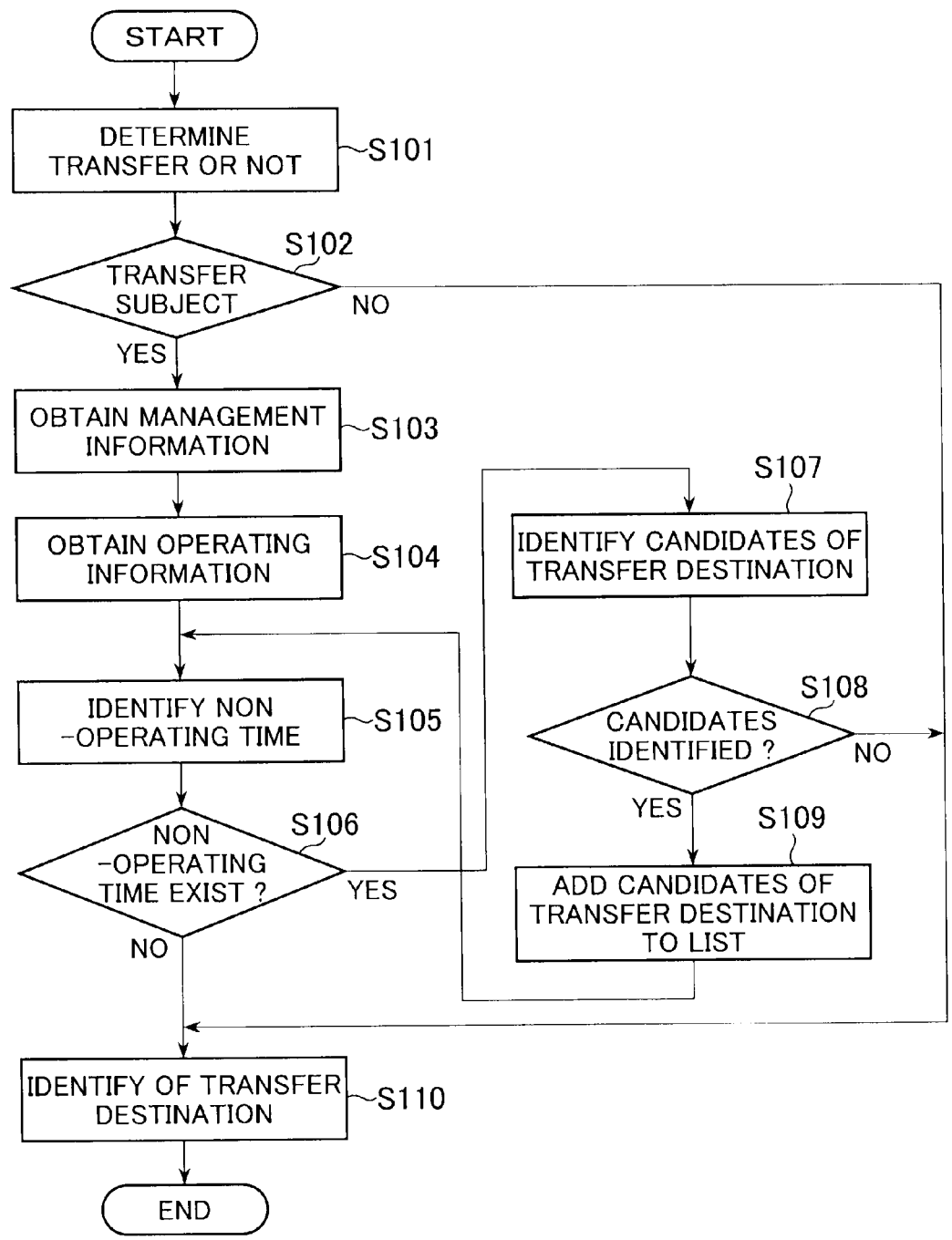
FIG. 9 is a flowchart of processes involved in the identification of a server that is to be the transfer destination.

Next, a series of operations related to the transfer of copies of medical information will be described with reference to FIG. 8 and FIG. 9. First, FIG. 8 will be referred to FIG. 8 is a diagram showing the flow of processes between servers involved in the transfer of copies of medical information.

(Step S10)

The medical-information transmission part 11A receives an instruction related to the transfer of medical information from the operator. Upon receiving this instruction, the medical-information transmission part 11A identifies the transfer subject from among the medical information stored in the medical-information memory 10A. Moreover, the medical-information transmission part 11A identifies the transfer destination server to which a copy of the identified transfer subject will be transferred. Detailed operations related to the identification of the transfer subject and the transfer destination server will be described with reference to FIG. 9. FIG. 9 is a flowchart of processes involved in the identification of a server that is to be the transfer destination.
(Step S101)

The medical-information transmission part 11A receives conditions related to the identification of the transfer subject from the operator, and identifies the transfer subject from among the medical information stored in the medical-information memory 10A. In other words, the medical-information transmission part 11A refers to the medical-information memory 10A, cross-checks each item of medical information with the conditions designated by the operator, and determines whether or not the item of medical information should be transferred.
(Step S102)

If an item of medical information is not a transfer subject (Step S102: N), the following processing is not performed for that item of medical information, and the process shifts to judging the next item of medical information.
(Step S103)

If an item of medical information is a transfer subject (Step S102: Y), the medical-information transmission part 11A outputs information for identifying that transfer subject (i.e., patient ID c20 and treatment information ID c21) to the management-information analysis part 12A. The management-information analysis part 12A refers to the data management information D20 stored in the management-information memory 22 and identifies instances of the facility ID c10 with which the information indicating the transfer subject is not associated. The management-information analysis part 12A identifies the servers corresponding to the identified facility ID c10 as servers in which the transfer subject is not managed and stored. The management-information analysis part 12A creates a list of these identified servers.

Moreover, the management-information analysis part 12A refers to the patient management information D30 stored in the management-information memory 22, and identifies the intra-facility ID c30 in each server corresponding to the notified patient ID c20. The management-information analysis part 12A associates the intra-facility ID c30 in each identified server with the list of servers created based on the data management information D20. The management-information analysis part 12A outputs the list of servers with which the intra-facility IDs c30 have been associated to the medical-information transmission part 11A.
(Step S104)

Moreover, the medical-information transmission part 11A instructs the operational-status analysis part 13A to output a list of servers operating during the non-operating time of the server 1A. The operational-status analysis part 13A refers to the operation information D10 stored in the operation-information memory 21.
(Step S105)

The medical-information transmission part 11A identifies the non-operating time of the server 1A based on the operation information D10.
(Step S106)

Next, the medical-information transmission part 11A determines whether or not the identified non-operating time is "0".
(Step S107)

If the identified non-operating time is not "0" (Step S106: Y), the operational-status analysis part 13A compares the identified non-operating time with the operating times of the other servers. Based on the results of this comparison, the operational-status analysis part 13A selects the servers operating for the longest time during the non-operating time as candidates.
(Step S109)

If candidates have been identified (Step S108: Y), the operational-status analysis part 13A creates a list of servers based on the identified candidates. If a list of servers has already been created (i.e., if other candidates have already been identified), the operational-status analysis part 13A adds the identified candidates to that list of servers. Next, the operational-status analysis part 13A subtracts the operating times of the servers identified as candidates from the non-operating time of the server 1A, so as to identify the time during which the server 1A and all of the servers included in the list of servers do not operate as the new non-operating time. Subsequently, the operational-status analysis part 13A repeats the processing related to the selection of candidates either until the non-operating time during which the server 1A and all of the servers selected as candidates do not operate becomes "0" (Step S106: N) or until there are no more candidates for servers operating for the longest time during the non-operating time (Step S108: N).
(Step S110)

When the selection of candidates is completed, the operational-status analysis part 13A outputs the list of servers selected as candidates to the medical-information transmission part 11A. The medical-information transmission part 11A identifies servers included in both the list of servers in which the transfer subject is not managed and stored as well as the list of servers operating during the non-operating time of the server 1A as transfer destination servers. The following description supposes that the medical-information transmission part 11A identifies the server 1B as the transfer destination server.
(Step S20)

Here, FIG. 8 will be referenced. The medical-information transmission part 11A creates a copy of the transfer subject, which is transferred to the medical-information recording part 14B of the server 1B.
(Step S31)

The medical-information recording part 14B receives the copy of the transfer subject from the medical-information transmission part 11A. The medical-information recording part 14B sets the cache flag 40 to "1", which indicates a copy transferred from another server, and stores the copy in the medical-information memory 10B.
(Step S32)

Moreover, the medical-information recording part 14B creates a row of data management information for the transfer subject based on the patient ID c20 and treatment information ID c21 indicating the medical information that is the transfer subject, as well as on the facility ID c10 indicating the server itself (i.e., the server 113). The medical-information recording part 14B adds the created row of data management information to the data management information D20 stored in the management-information memory 22.
(Referencing of Medical Information)

Figure 10:
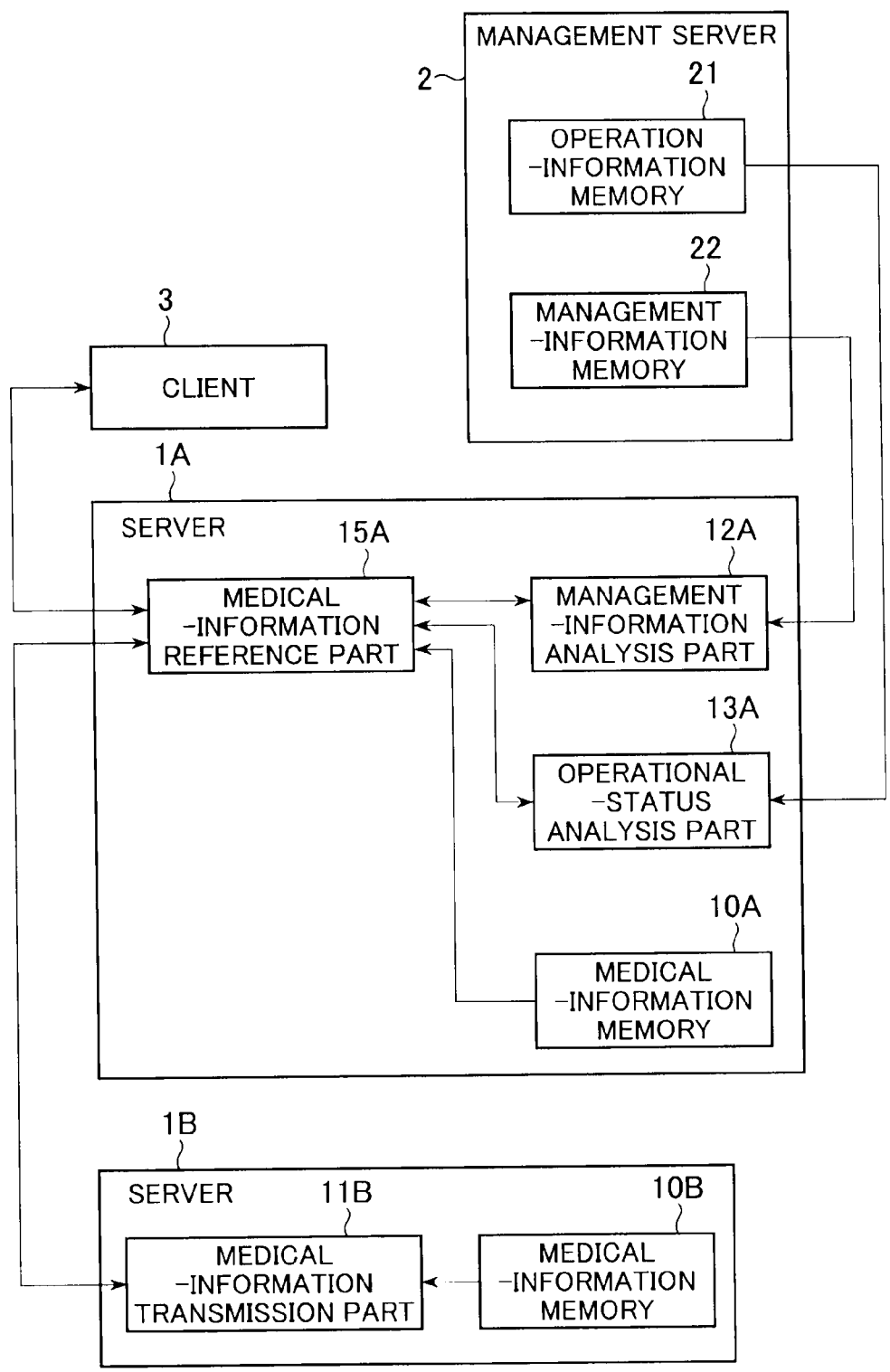
FIG. 10 is a block diagram of a medical-information management system focusing on the referencing of medical information.

Next, configurations that operate in cases of referencing medical information will be described with reference to FIG. 10. FIG. 10 is a block diagram of a medical-information management system focusing on the referencing of medical information. FIG. 10 shows a case of referring to medical information stored in the server 1B from the server 1A. In FIG. 10, the medical-information reference part 15A, the management-information analysis part 12A, the operational-status analysis part 13A, and the medical-information memory 10A respectively represent the medical-information reference part 15, the management-information analysis part 12, the operational-status analysis part 13, and the medical-information memory 10 included in the server 1A. Moreover, the medical-information transmission part 11B and the medical-information memory 10B respectively represent the medical-information transmission part 11 and the medical-information memory 10 included in the server 1B.

The medical-information reference part 15A receives an instruction related to the output of medical information (i.e. a retrieval request) from the client 3. Hereinafter, the medical information for which an instruction for output has been issued may be also referred to as the "retrieval subject". Upon receiving this retrieval request, the medical-information reference part 15A searches the medical-information memory 10A of the server itself and identifies the retrieval subject.

If a retrieval subject is identified from among the medical information stored in the medical-information memory 10A of the server itself, the medical-information reference part 15A reads out the retrieval subject from the medical-information memory 10A and outputs it to the client 3.

If no retrieval subject is identified from among the medical information stored in the medical-information memory 10A, the medical-information reference part 15A outputs information indicating the retrieval subject (i.e., the patient ID c20 and the treatment information ID c21) to the management-information analysis part 12A. As a response, the medical-information reference part 15A receives a list of servers in which the retrieval subject is managed and stored from the management-information analysis part 12A. Moreover, the medical-information reference part 15A causes the operational-status analysis part 13A to output a list of servers operating at that time. Operations of the management-information analysis part 12A and the operational-status analysis part 13A will be described later.

The medical-information reference part 15A identifies servers included in both the list of servers in which the retrieval subject is managed and stored as well as the list of servers operating at that time as transfer source servers. In other words, the transfer source servers indicate servers that are operating at that time and in which the retrieval subject is managed and stored. The following description supposes that the medical-information reference part 15A identifies the server 1B as the transfer source server.

The medical-information reference part 15A instructs the medical-information transmission part 11B of the server 1B to transfer the retrieval subject.

When the instruction is received from the medical-information reference part 15A, the medical-information transmission part 11B searches the medical-information memory 10B to read out the retrieval subject from among the medical information stored in the medical-information memory 10B. The medical-information transmission part 11B transfers the read-out retrieval subject to the medical-information reference part 15A. At this time, based on the instruction from the medical-information reference part 15A, the medical-information transmission part 11B may operate to determine whether the retrieval subject has been created within the server or is a copy transferred from another server before searching the medical-information memory 1013. As a result, it becomes possible to limit the search range in advance and shorten the search time. Upon receiving the retrieval subject transferred from the medical-information transmission part 11B, the medical-information reference part 15A outputs the retrieval subject to the client 3 that is the source of the request for the output of medical information.

Next, detailed operations of the management-information analysis part 12A and the operational-status analysis part 13A will be described.

The management-information analysis part 12A receives information indicating the medical information (i.e., the patient ID c20 and the treatment information ID c21) from the medical-information reference part 15A. The management-information analysis part 12A refers to the data management information D20 stored in the management-information memory 22, to identify servers in which the medical information is managed and stored, to create a list of those servers.

Moreover, the management-information analysis part 12A refers to the patient management information D30 stored in the management-information memory 22, to identify the intra-facility ID c30 in each server corresponding to the notified patient ID c20, to associate the IDs with the created list of servers. The management-information analysis part 12A outputs the list of servers with which the intra-facility IDs c30 have been associated to the medical-information reference part 15A. As a result, it becomes possible for the medical-information reference part 15A to identify servers in which desired medical information is stored. Furthermore, this list of servers represents the "fourth group".

The operational-status analysis part 13A receives an instruction from the medical-information reference part 15A to identify other operating servers other than the server 1A. Upon receiving this instruction, the operational-status analysis part 13A compares the operation information D10 stored in the operation-information memory with the time at which the instruction was received from the medical-information reference part 15A, to identify servers operating during that time. The operational-status analysis part 13A creates a list of the identified servers, and outputs this list to the medical-information transmission part 11A. Furthermore, this list of servers represents the "third group".

Figure 11:
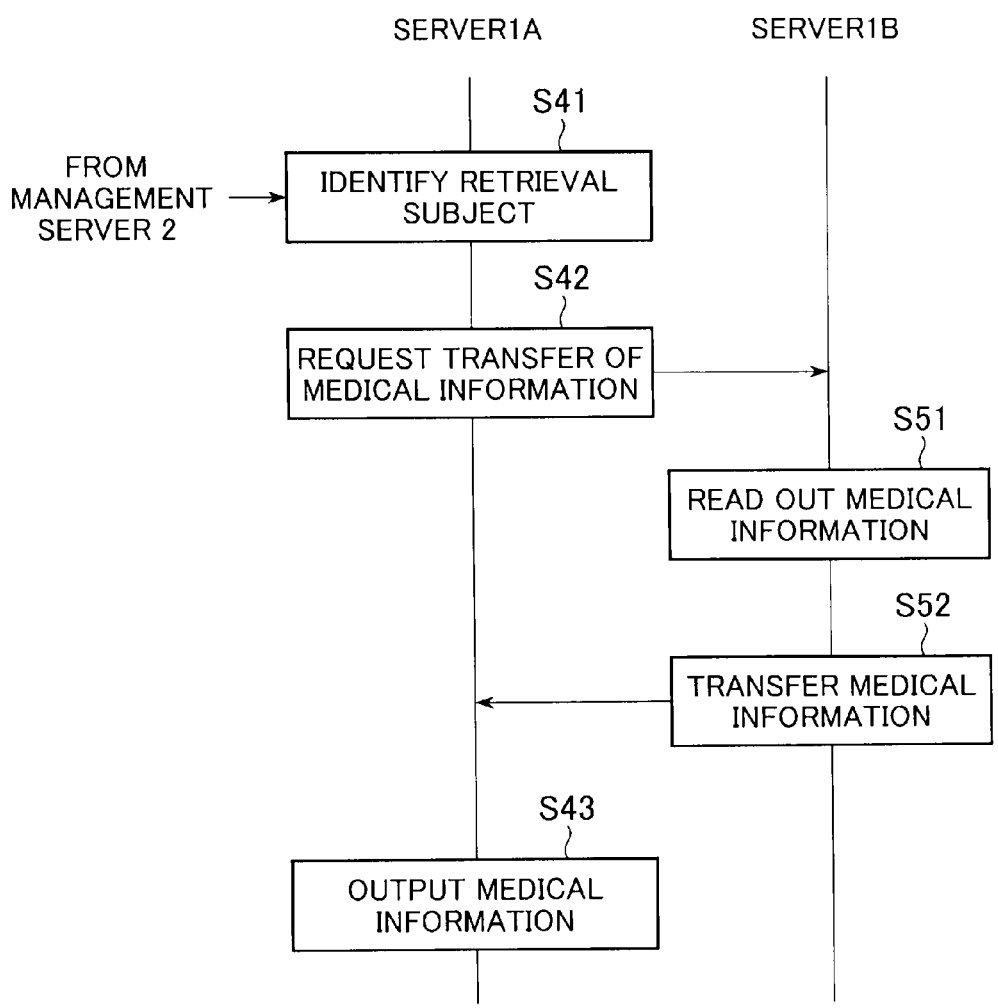
FIG. 11 is a diagram showing the flow of processes between servers involved in the referencing of medical information.

Next, a series of operations related to the referencing of medical information will be described with reference to FIG. 11. FIG. 11 is a diagram showing a flow of processes between servers involved in the referencing of medical information.
(Step S41)

The medical-information reference part 15A receives an instruction from the client 3 to output medical information (i.e., the retrieval subject). Upon receiving this instruction, the medical-information reference part 15A searches the medical-information memory 10A and identifies the retrieval subject. If a retrieval subject is identified from among the medical information stored in the medical-information memory 10A, the medical-information reference part 15A reads out the retrieval subject from the medical-information memory 10A and outputs it to the client 3.

If no retrieval subject is identified from among the medical information stored in the medical-information memory 10A, the medical-information reference part 15A outputs information indicating the retrieval subject (i.e., the patient ID c20 and the treatment information ID c21) to the management-information analysis part 12A.

The management-information analysis part 12A receives the information indicating the medical information (i.e., the patient ID c20 and the treatment information ID c21) from the medical-information reference part 15A. The management-information analysis part 12A refers to the data management information D20 stored in the management-information memory 22, to identify servers in which the medical information is managed and stored, to create a list of those servers.

Moreover, the management-information analysis part 12A refers to the patient management information D30 stored in the management-information memory 22 to identify the intra-facility ID c30 in each server corresponding to the notified patient ID c20, and associate the IDs with the created list of servers. The management-information analysis part 12A outputs the list of servers with which the intra-facility IDs c30 have been associated to the medical-information reference part 15A.

Moreover, the medical-information reference part 15A instructs the operational-status analysis part 13A to output a list of servers operating at that time. Upon receiving this instruction, the operational-status analysis part 13A compares the operation information D10 stored in the operation-information memory 21 with the time at which the instruction was received from the medical-information reference part 15A, to identify servers operating during that time. The operational-status analysis part 13A creates a list of the identified servers and outputs the list to the medical-information transmission part 11A.

As a response, the medical-information reference part 15A receives a list of servers in which the retrieval information is managed and stored from the management-information analysis part 12A. Moreover, the medical-information reference part 15A causes the operational-status analysis part 13A to output the list of servers operating at that time.

The medical-information reference part 15A identifies servers included in both the list of servers in which the retrieval subject is managed and stored as well as the list of servers operating at that time as the transfer source servers. The following description supposes that the medical-information reference part 15A identifies the server 1B as the transfer source server.
(Step S42)

The medical-information reference part 15A instructs the medical-information transmission part 1113 of the server 1B to transfer the retrieval subject.
(Step S51)

The medical-information transmission part 11B receives the instruction from the medical-information reference part 15A, searches the medical-information memory 1013, and reads out the retrieval subject from among the medical information stored in the medical-information memory 10B.
(Step S52)

The medical-information transmission part 11B reads out the read-out retrieval subject from the medical-information memory 10B and transfers it to the medical-information reference part 15A.
(Step S43)

Upon receiving the retrieval subject transferred from the medical-information transmission part 1113, the medical-information reference part 15A outputs the retrieval subject to the client 3 that is the source of the request for the output of medical information.

Figure 12:
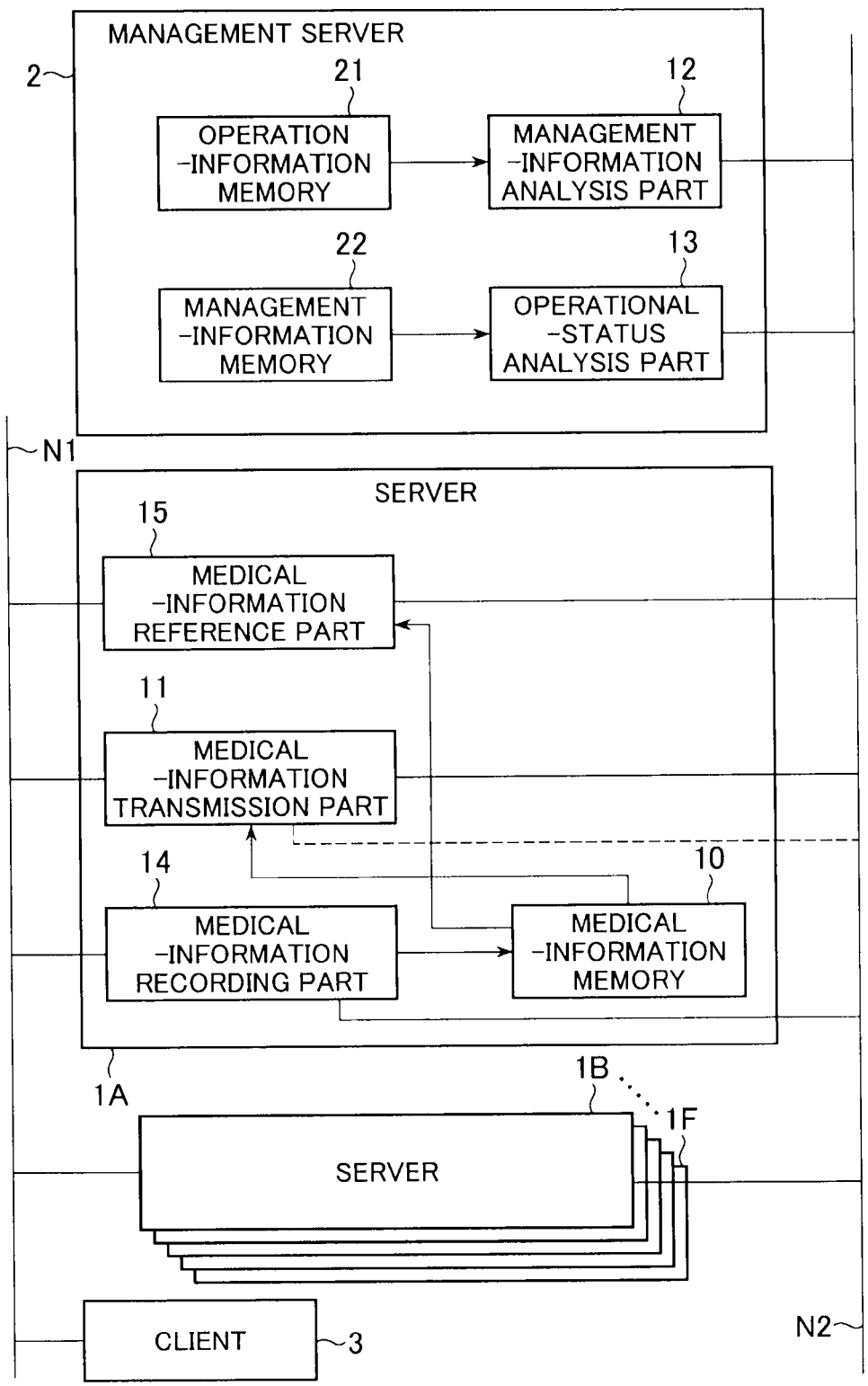
FIG. 12 is a block diagram showing an example of a medical-information management system according to an embodiment.

Furthermore, the management-information analysis part 12 and the operational-status analysis part 13 only have to be able to output various information to the medical-information transmission part 11 and the medical-information reference part 15 as described above, and do not necessarily have to be included in the servers 1A-1F. For example, FIG. 12 shows an example in which the management-information analysis part 12 and the operational-status analysis part 13 are included in the management server 2. In this case, the management-information analysis part 12 and the operational-status analysis part 13 outputs various information via the network N2 to the medical-information transmission part 11 and the medical-information reference part 15. Of course, the management-information analysis part 12 and the operational-status analysis part 13 may be included in independent servers. In this case, the management-information analysis part 12 and the operational-status analysis part 13 transmit and receive various information to and from each of the operation-information memory 21, the management-information memory 22, the medical-information transmission part 11, and the medical-information reference part 15 via the network N2. Moreover, if the connective relationships of each configuration are maintained, the locations of the operation-information memory 21 and the management-information memory 22 are not limited, and the operation-information memory 21 and the management-information memory 22 may be provided in any one of, or part of, or all of the servers 1A-1F. Furthermore, if providing the operation-information memory 21 and the management-information memory 22 to multiple servers, it is advisable to provide a configuration for synchronizing the information stored in the operation-information memory 21 and the management-information memory 22 among the multiple servers.

Moreover, in the above descriptions, the transfer destination servers are identified based on the operating times. In addition to the operating times, the transfer destination servers may be identified based on the operating period (i.e., the period from the date on which the server starts operating to the date on which the operation ends). This operating period can be identified based on the start date c13 and the end date c14 included in the operation information. By thus considering the operating period, it becomes possible to implement operations so that, for example, the server 1B of FIG. 4 ends operation on 2020/12/31 while information is acquired from the server 1F, from 2021/01/01 onward.

As described above, the medical-information transmission part 11A transfers a copy of the transfer subject to servers operating during the non-operating time of the server 1A so that servers manage and store the information. As a result, even during the non-operating time of the server 1A, it becomes possible to acquire and reference copies of medical information stored in the server 1A from other servers. Moreover, because it is not necessary to manage and store copies of the transfer subject in all of the servers, it becomes possible to ease the lack of volume in storage area caused by the storage of copies.

Second Embodiment

Figure 13:
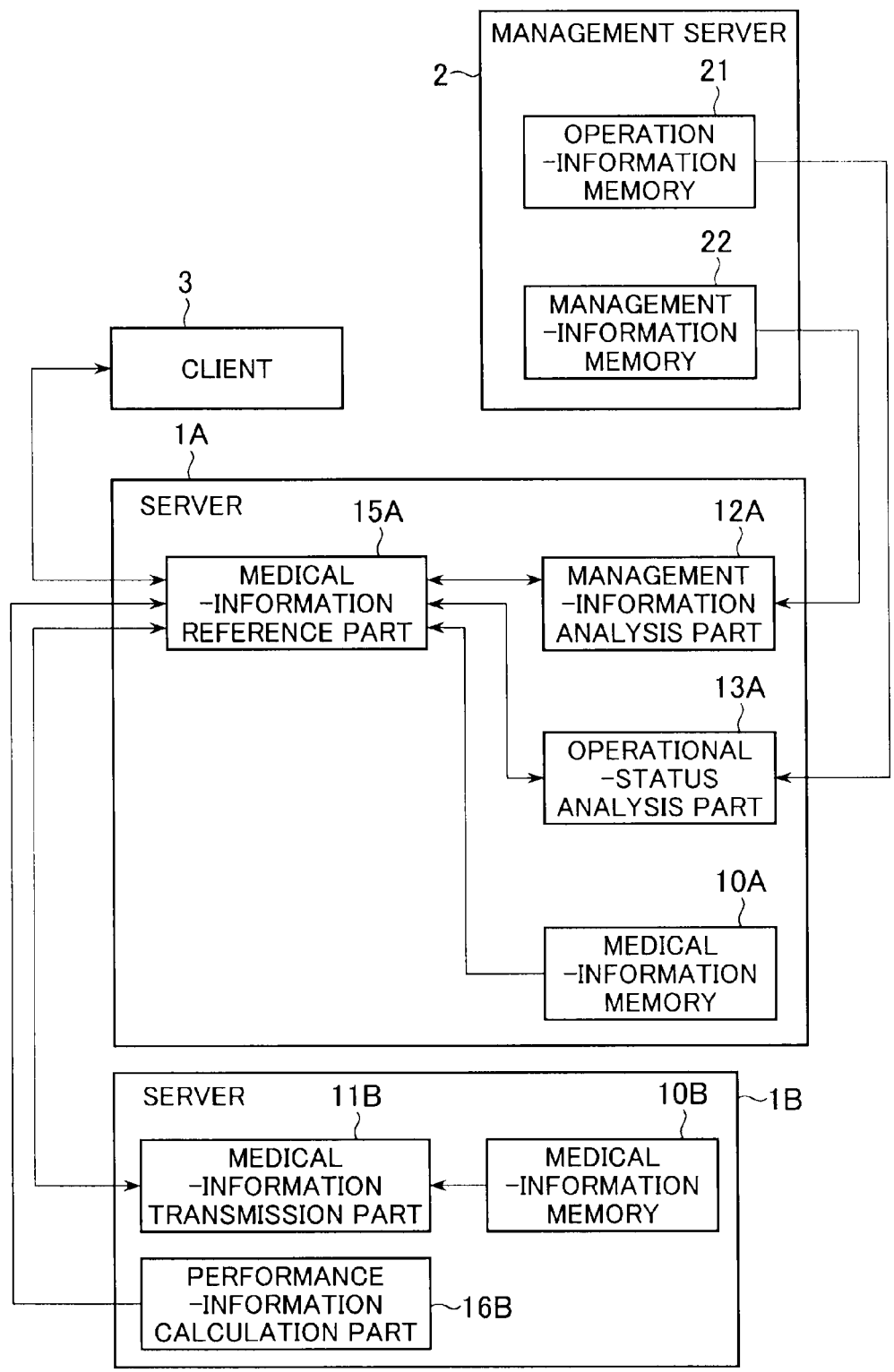
FIG. 13 is a block diagram of a medical-information management system according to a second embodiment focusing on the referencing of medical information.

During the referencing of medical information, the medical-information management system according to the second embodiment transfers the medical information that is the retrieval subject to a server with a low processing load. For this reason, the servers 1A-1F according to the present embodiment include a performance-information calculation part 16 in addition to the configurations of the servers 1A-1F: according to the first embodiment. In the following, the configurations of the medical-information management system according to the present embodiment will be described with a focus on configurations different from those of the first embodiment, with reference to FIG. 13. FIG. 13 is a block diagram of the medical-information management system according to the present embodiment with a focus on the referencing of medical information. FIG. 13 shows a case in which medical information stored in the server 1B is referenced from the server 1A. In FIG. 13, the medical-information reference part 15A, the management-information analysis part 12A, the operational-status analysis part 13A, and the medical-information memory 10A respectively represent the medical-information reference part 15, the management-information analysis part 12, the operational-status analysis part 13, and the medical-information memory 10 included in the server 1A. Moreover, the medical-information transmission part 11B, the medical-information memory 10B, and the performance-information calculation part 16B respectively represent the medical-information transmission part 11, the medical-information memory 10, and the performance-information calculation part 16 of the server 1B.

When an instruction is received from the medical-information reference part 15A, the performance-information calculation part 16B calculates the processing load of the server 1B at the time of receiving the instruction. As a specific example, the performance-information calculation part 16B calculates the processing load of the CPU of the server 1B based on the CPU usage rate of the server 1B. Moreover, based on the allowable volume of input/output data of the network card of the server 1B as well as the size of the data to be input and output to and from the network card, the performance-information calculation part 16B calculates the I/O load of the network card. In this way, the performance-information calculation part 16B calculates the processing load involved in processing for reading out and transferring a retrieval subject from the medical-information memory 10B. The performance-information calculation part 16B outputs information indicating the calculated processing load to the medical-information reference part 15A.

The medical-information reference part 15A receives an instruction from the client 3 to output the medical information (i.e., the retrieval subject). Upon receiving this instruction, the medical-information reference part 15A searches the medical-information memory 10A to identify the retrieval subject. If a retrieval subject is identified from among the medical information stored in the medical-information memory 10A, the medical-information reference part 15A reads out the retrieval subject from the medical-information memory 10A and outputs it to the client 3. This operation is the same as that in the first embodiment.

If no retrieval subject is identified from among the medical information stored in the medical-information memory 10A, the medical-information reference part 15A outputs information indicating the retrieval subject (i.e., the patient ID c20 and the treatment information ID c21) to the management-information analysis part 12A. As a response, the medical-information reference part 15A receives a list of servers in which the retrieval subject is managed and stored from the management-information analysis part 12A. Moreover, the medical-information reference part 15A causes the operational-status analysis part 13A to output a list of servers operating at this time. Furthermore, the operations of the management-information analysis part 12A and the operational-status analysis part 13A in this case are the same as those in the first embodiment.

The medical-information reference part 15A identifies servers included in both the list of servers in which the retrieval subject is managed and stored as well as the list of servers operating at that time as transfer source servers.

If multiple transfer source servers have been identified, the medical-information reference part 15A instructs the performance-information calculation parts 16 of the transfer source servers to provide notification of the processing loads. As a response, the medical-information reference part 15A receives information indicating the respective processing load of each server from the respective performance-information calculation part 16 of each transfer source server. The medical-information reference part 15A compares the processing loads received from each server, and identifies the server with the lowest processing load as the new transfer source server. This description supposes that the medical-information reference part 15A identifies the server 1B as the new transfer source server. The medical-information reference part 15A instructs the medical-information transmission part 11B of the server 1B to transfer the retrieval subject. Furthermore, a configuration may be used in which the process of identifying these transfer source servers is executed by the operational-status analysis part 13A instead of the medical-information reference part 15A, and the medical-information reference part 15A receives the results (i.e., the transfer source servers) from the operational-status analysis part 13A and operates. Moreover, in addition to instances of referencing medical information, the transfer destination servers may be identified based on the information indicating processing loads when transferring copies of medical information, for example.

When the instruction is received from the medical-information reference part 15A, the medical-information transmission part 11B searches the medical-information memory 10B, and reads out the retrieval subject from among the medical information stored in the medical-information memory 10B. The medical-information transmission part 11B reads out the read-out retrieval subject from the medical-information memory 10B and transfers it to the medical-information reference part 15A. Upon receiving the retrieval subject transferred from the medical-information transmission part 11B, the medical-information reference part 15A outputs the retrieval subject to the client 3 that is the source of the request for the output of medical information.

As described above, according to the medical-information management system according to the present embodiment, if there are multiple transfer source servers when referencing medical information, the medical-information reference part 15A instructs the server with the lowest processing load (in other words, the server with a quick response time) to transfer the medical information. As a result, in addition to the operational effects of the medical-information management system according to the first embodiment, it also becomes possible to prevent the concentration of processes related to the retrieval of medical information in a specific server.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical-information management system, connected via a network to a plurality of servers having medical-information memories storing medical information, which manages the medical information by distributing the medical information of a plurality of medical facilities to the plurality of servers, the medical-information management system comprising:

an operating-time-information memory that stores the respective operating times of the plurality of servers;

a management-information memory that stores management information indicating the servers storing the medical information;

an operational-status analysis part configured to provide notification of other servers different from a first server based on information related to the operating times; and a medical-information transmission part configured to determine a second server for temporarily saving the medical information stored in the first server from among the notified other servers, and transmit the medical information stored in the medical-information memory of the first server to the second server.

2. The medical-information management system according to claim 1, wherein the medical-information transmission part is configured to estimate the medical information that has a high probability of being used, to transmit the estimated medical information to the second server.

3. The medical-information management system according to claim 2, wherein, the medical-information transmission part is configured to estimate the medical information that has a high probability of being used based on the severity of the symptoms of the patient corresponding to the medical information, or on the volume of information included in the medical information.

4. The medical-information management system according to claim 1, wherein
the second server is configured to store the medical information transmitted from the first server to be distinguished from the medical information stored in the second server, and
the second server further comprises a retrieval part configured to retrieve the medical information transmitted from the first server based on a retrieval request from an external source.

5. The medical-information management system according to claim 1, wherein the medical-information transmission part is configured to determine processing-load information of each of the plurality of servers to determine the second server based on the processing-load information.

6. The medical-information management system according to claim 5, wherein the medical-information transmission part is configured to determine a server with a quick response time as the second server based on the processing-load information.

7. A medical-information management system, comprising:
a plurality of medical-information servers comprising medical-information memories storing medical information; and
a management information server that manages information of a plurality of medical facilities and stores management information that indicates the medical-information servers in which the medical information is stored, wherein
at least one of the medical-information servers and the management information server comprises:
an operating-time-information memory that stores information regarding the operating times of the plurality of medical-information servers;
an operational-status analysis part configured to provide notification of other servers different from a first medical-information server based on the information regarding operating times and
a medical-information transmission part configured to determine a second medical-information server for temporarily saving the medical information stored in the first medical-information server from among the notified other servers, and transmit the medical information stored in the medical-information memory of the first medical-information server to the second medical-information server.

8. The medical-information management system according to claim 1, wherein
the operational-status analysis part is configured to compare the operating time of a first server included in the plurality of servers with the operating times of other servers other than the first server, and provide notification of a first group that includes servers operating at times when the first server is not operating from among the other servers, and
the medical-information transmission part is configured to transmit a first item of medical information stored in the medical-information memory to a second server included in the first group.

9. The medical-information management system according to claim 8, further comprising:
a management-information analysis part configured to, based on the management information, provide notification of a second group including servers in which the first item of medical information is not stored from among the plurality of servers, wherein
the medical-information transmission part is configured to determine a server included in both the first group and the second group as the second server.

10. The medical-information management system according to claim 9, further comprising:
a medical-information reference part configured to receive retrieval requests for second item of medical information, wherein
based on the operating times of the plurality of servers, the operational-status analysis part is configured to provide notification of a third group including servers operating at the time of receiving the request,
based on the management information, the management-information analysis part is configured to provide notification of a fourth group including servers in which the second item of medical information is stored, and
in response to receiving the retrieval request, the medical-information reference part is configured to identify one server included in both the third group and the fourth group as a third server, and cause the second item of medical information to be transmitted to the third server.

11. The medical-information management according to claim 10, wherein
the servers comprise performance-information calculation parts configured to calculate the processing load of the server itself, and
if there are a plurality of servers included in both the third group and the fourth group, the medical-information reference part is configured to cause the performance-information calculation parts of the servers included in both to calculate the processing loads, and to compare the processing loads, to identify the server with the lowest processing load as the third server.

12. The medical-information management server according to claim 8, wherein
the medical-information memory stores the medical information associated with the access count of the medical information, and
from the medical information stored in the medical-information memory, the medical-information transmission part is configured to identify the medical information for which the access count is equal to or greater than a prescribed threshold value as the first item of medical information.

13. The medical-information management system according to claim 8, wherein
based on at least part of the information included in the medical information, the medical-information transmission part is configured to identify the first item of medical information from among the medical information stored in the medical-information memory.

14. A medical-information management method based on a medical-information management system, connected via a network to a plurality of servers having medical-information memories storing medical information, which manages the medical information by distributing a plurality of items of the medical information to the plurality of servers, the medical-information management method comprising:

comparing the operating time of a first server included in the plurality of servers with the operating times of other servers other than the first server, based on the pre-stored operating times of multiple servers, to identify a first group including servers operating when the first server is not operating from among the other servers;

identifying a second group from among the plurality of servers, based on pre-stored management information indicating the servers storing the medical information, the second group including servers in which a first item of medical information is not stored;

identifying a server included in both the first group and the second group as the second server, to transmit the first item of medical information to the second server;

identifying a third group based on the operating times of the plurality of servers, upon receiving a retrieval request for the first item of medical information, the third group including servers operating at the time at which the request was received;

identifying a fourth group based on the management information, the fourth group including servers in which the first item of medical information is stored; and identifying one server included in both the third group and the fourth group as the third server, to transmit the first item of medical information to the third server.

15. A medical-information management system, connected via a network to a plurality of servers having medical-information memories storing medical information, which manages the medical information by distributing a plurality of the medical information to the plurality of servers, the medical-information management system comprising:

an operating-time-information memory that stores the respective operating times of each of the plurality of servers;

a management-information memory that stores management information indicating the servers storing the medical information; and an operational-status analysis part configured to compare the operating time of a first server included in the plurality of servers with the operating time of other servers other than the first server, and provide notification of a second server operating when the first server is not operating from among the other servers, wherein the first server comprises a medical-information transmission part configured to transmit a first item of medical information stored in the medical-information memory to the second server.

\* \* \* \* \*